(12) United States Patent
Van Nortwick et al.

(10) Patent No.: US 8,523,915 B2
(45) Date of Patent: Sep. 3, 2013

(54) FRICTION SET SCREW FOR USE WITH SPINAL IMPLANT SYSTEMS

(75) Inventors: Matthew Van Nortwick, Memphis, TN (US); Christopher Nelson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 210 days.

(21) Appl. No.: 12/964,207

(22) Filed: Dec. 9, 2010

(65) Prior Publication Data

US 2012/0150232 A1    Jun. 14, 2012

(51) Int. Cl.
*A61B 17/70* (2006.01)

(52) U.S. Cl.
USPC .......................................................... 606/270

(58) Field of Classification Search
USPC .................................. 606/264–275, 300–308
See application file for complete search history.

(56) References Cited

U.S. PATENT DOCUMENTS

| | | | | |
|---|---|---|---|---|
| 5,797,911 | A * | 8/1998 | Sherman et al. | 606/270 |
| 6,296,642 | B1 * | 10/2001 | Morrison et al. | 606/305 |
| 6,843,791 | B2 * | 1/2005 | Serhan | 606/272 |
| 7,204,838 | B2 * | 4/2007 | Jackson | 606/270 |
| 7,641,674 | B2 * | 1/2010 | Young | 606/270 |
| 8,080,040 | B2 * | 12/2011 | Miller | 606/272 |
| 2010/0057126 | A1 * | 3/2010 | Hestad | 606/246 |
| 2010/0114168 | A1 * | 5/2010 | Miller | 606/264 |

* cited by examiner

*Primary Examiner* — Ellen C Hammond

(57) ABSTRACT

A set screw for use in association with spinal implant assemblies. The set screw includes a threaded base portion extending along a longitudinal axis and formed of a first material, and a friction member extending from a distal end of the threaded base portion and formed of a second material different from the first material. In one embodiment, the spinal implant assembly includes a connector member having a passage and an opening in communication with the passage, and an elongate support member positioned within the passage of the connector member. The set screw is threadedly engaged to the connector member and at least partially positioned within the opening, with a distal end portion of the friction member extending into the passage and compressed against an outer surface of the elongate support member to inhibit movement of the elongate support member within the passage.

23 Claims, 6 Drawing Sheets

FRICTION SET SCREW FOR USE WITH SPINAL IMPLANT SYSTEMS

BACKGROUND

The present invention relates generally to set screws for use with spinal implant systems to attach an elongate support member to bone, and more particularly relates to a set screw having a friction member positioned at a distal end of the set screw which frictionally engages an elongate support member positioned within a connector device to prevent movement of the elongate support member relative to the connector device.

Several techniques and systems have been developed for fixing and/or stabilizing the spinal column. In one type of system, a connecting element such as an elongate spinal rod is disposed longitudinally along a length of the spinal column or along several vertebrae of the spinal column. The spinal rod is attached to various vertebrae by way of a number of bone anchors. A variety of bone anchors can be used to attach the spinal rod to the vertebrae. For example, a bone screw can be threaded into one or more aspects of a vertebra such as, for example, the pedicle region of a vertebra. Additionally, a hook can be wrapped about a portion of a vertebra such as, for example, the lamina region of a vertebra. The bone anchor typically includes a connector portion including a passage or channel sized to receive the spinal rod, and a threaded opening in communication with the passage for receipt of a set screw. The set screw is threaded through the opening and into abutment against the spinal rod to capture the spinal rod within the passage. However, the force applied to the spinal rod by the set screw is sometimes insufficient to prevent rotational or translational movement of the spinal rod relative to the connector portion of the bone anchor, and may also exert excessive force or stress onto the connector member or the spinal rod and/or penetrate or cut into the spinal rod, thereby weakening or negatively affecting the structural integrity of the spinal rod and/or the connector member.

Thus, there remains a need for an improved set screw for use with a spinal implant system. The present invention satisfies this need and provides other benefits and advantages in a novel and unobvious manner.

SUMMARY

The present invention relates generally to a friction set screw for use with spinal implant systems. While the actual nature of the invention covered herein can only be determined with reference to the claims appended hereto, certain forms of the invention that are characteristic of the preferred embodiments disclosed herein are described briefly as follows.

In one form of the present invention, a set screw is provided for use in association with spinal implant systems. The set screw includes a threaded base portion extending along a longitudinal axis and formed of a first material, and a friction member extending from a distal end of the threaded base portion and formed of a second material different from the first material.

In another form of the present invention, the set screw is used in association with a spinal implant assembly including a connector member including a passage and an opening in communication with the passage, and an elongate support member positioned within the passage of the connector member. The set screw is threadedly engaged to the connector member and at least partially positioned within the opening with a distal end portion of the friction member extending into the passage and compressed against an outer surface of the elongate support member to inhibit movement of the elongate support member within the passage.

It is one object of the present invention to provide a friction set screw for use with spinal implant systems. Further embodiments, forms, features, aspects, benefits, objects, and advantages of the present application will become apparent from the detailed description and figures provided herewith.

DESCRIPTION OF THE ILLUSTRATED EMBODIMENTS

Figure 1:
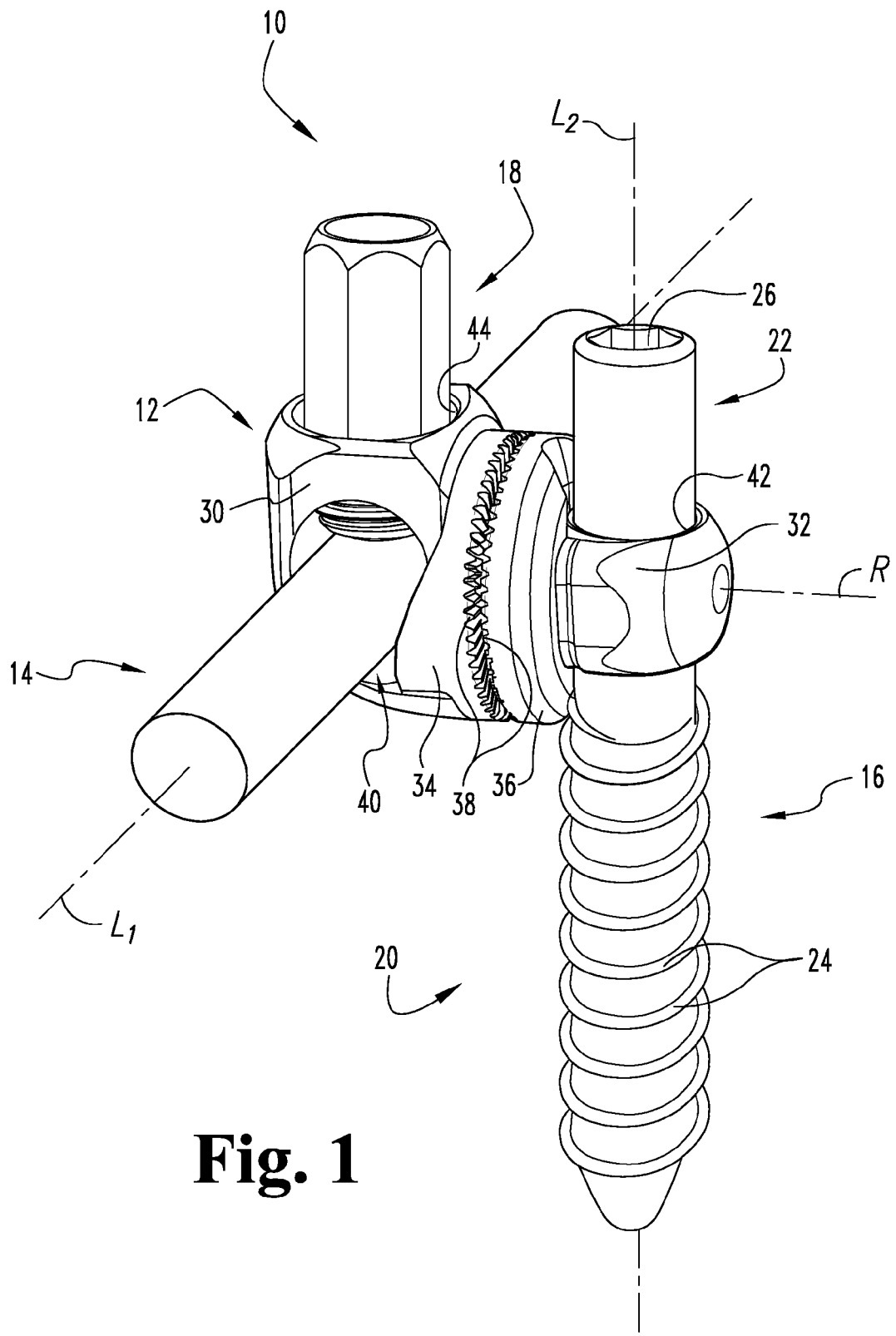
FIG. 1 is a perspective view of one embodiment of a spinal implant system.

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates.

Figure 2:
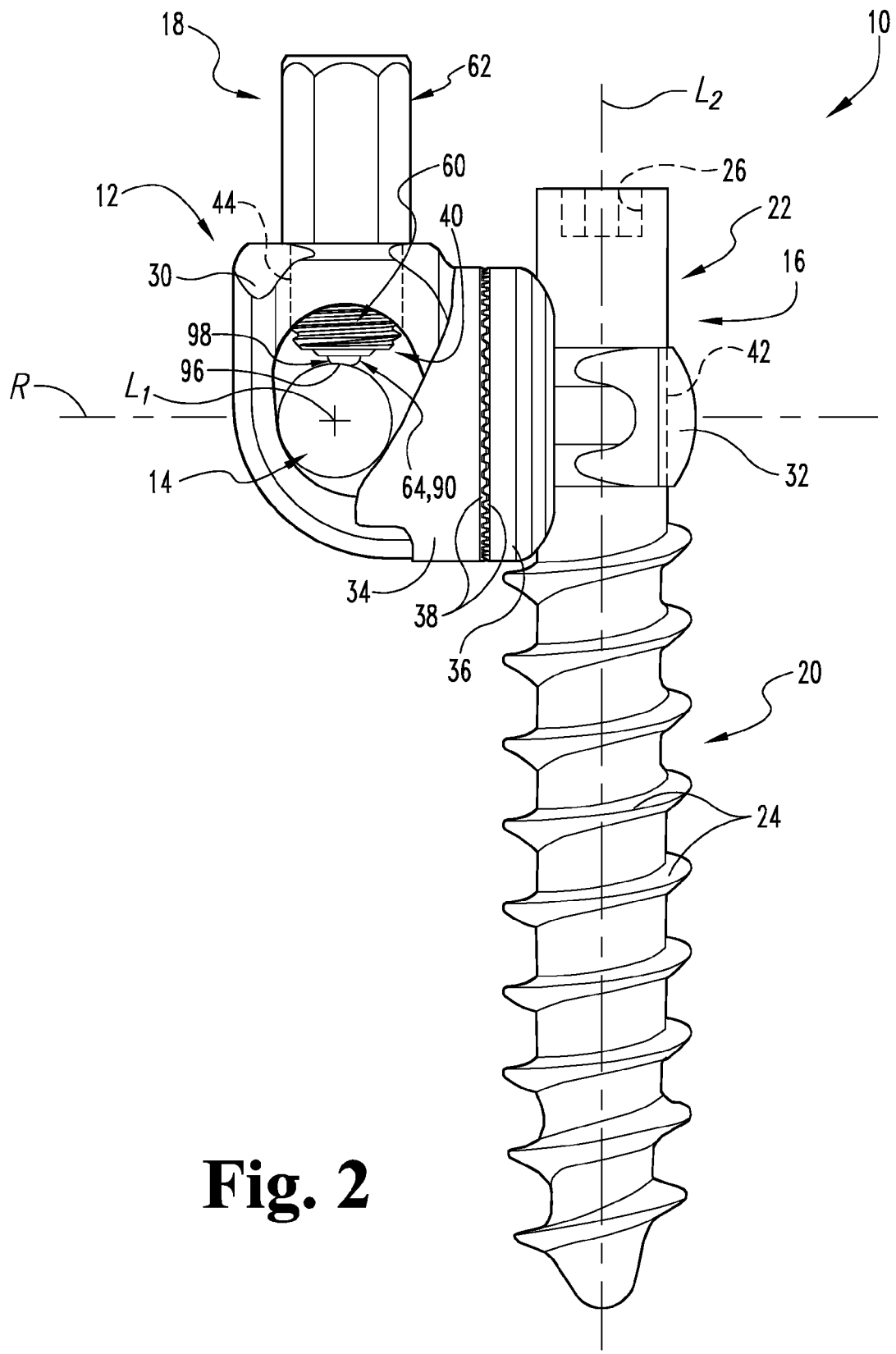
FIG. 2 is a side elevational view of the spinal implant system of FIG. 1.

Referring collectively to FIGS. 1 and 2, shown therein is a spinal stabilization system 10 according to one embodiment of the present invention. The spinal stabilization system 10 generally includes an adjustable spinal connector assembly 12 extending generally along a rotational axis R and which is configured to interconnect an elongate support member 14 extending generally along a first longitudinal axis $L_1$ with a bone anchor member 16 extending generally along a second longitudinal axis $L_2$ that is laterally offset from and arranged transverse to the first longitudinal axis $L_1$, and a set screw member 18 according to one form of the present invention for use in association with the spinal stabilization system 10.

As will be discussed in greater detail below, in the illustrated embodiment, the elongate support member 14 comprises a spinal rod and the bone anchor member 16 comprises a bone screw. However, other types and configurations of the elongate support member 14 and the bone anchor member 16 are also contemplated for use in association with the present invention. Additionally, it should be understood that the connector assembly 12 may be used to interconnect various types and configurations of spinal implants or devices, and is not limited to interconnecting a bone anchor member with an elongate support member. For example, the connector assembly 12 may also be used to interconnect a pair of elongate support members 14, or to interconnect other implants or devices. It should also be understood that the connector assembly 12 may be used in fields outside of the spinal field including, for example, in fixation or stabilization systems that are attached to other bony structures including the pelvis, the skull and/or the occiput, long bones, or other bony structures that would occur to those having ordinary skill in the art.

In the illustrated embodiment, the elongate support member 14 is configured as a spinal rod including a substantially smooth outer surface defining a circular outer cross section having a substantially uniform outer diameter. However, it should be understood that the elongate support member 14 may be provided with other cross sectional shapes, and the outer surface may be roughened (e.g., via knurling or threading) or otherwise textured to facilitate secure connection with the connector assembly 12. It should also be understood that other types and configurations of elongate support members are also contemplated for use in association with the present invention including, for example, bars, elongate plates, wires, tethers, or any other type of elongate support member know to those having ordinary skill in the art.

In the illustrated embodiment, the bone anchor member 16 generally includes a distal bone engaging portion 20 and a proximal connecting portion 22. In one particular embodiment, the bone anchor member 16 is configured as a bone screw, and more particularly as a Schanz-type bone screw where the bone engaging portion 20 is configured as a threaded shank including bone engaging threads 24 adapted for anchoring in bone, and where the proximal connecting portion 22 is configured as a cylindrical-shaped head or post including a substantially circular and smooth outer surface having a generally uniform outer diameter. However, it should be understood that the proximal connecting portion 22 may be provided with other shapes and configurations and may be roughened or textured to facilitate secure connection with the connector assembly 12. The proximal connecting portion 22 is also provided with a tool engaging feature 26 configured for releasable engagement with a driver instrument (not shown) to facilitate driving of the bone anchor member 16 into bone. It should also be understood that other types and configurations of bone screws are also contemplated including, for example, bone screws having other thread configurations and/or other types of proximal connecting portions. Additionally, other types and configurations of bone anchor members are also contemplated for use in association with the present invention including, for example, hooks, pins, bolts, clamps, staples, interbody devices, or any other type of bone anchor device know to those having ordinary skill in the art.

In the illustrated embodiment, the connector assembly 12 generally includes a first connector member 30 configured for coupling with the elongate support member 14, a second connector member 32 configured for coupling with the bone anchor member 16, a first washer member 34 associated with the first connector member 30, a second washer member 36 associated with the second connector member 32, and with the set screw member 18 threadedly engaged with the first connector member 30. The first and second washer members 34, 36 include interdigitating or intermeshing spline elements 38 configured to aid in selectively preventing relative rotational movement between the first and second connector members 30, 32 about the rotational axis R.

The first connector member 30 includes a first passage 40 sized and configured to receive the elongate support member 14 therein, and a threaded opening 44 in communication with the first passage 40 and configured for threading receipt of the set screw member 18. The second connector member 32 includes a second passage 42 sized and configured to receive a proximal portion of the bone anchor member 16 therein. The connector assembly 12 is configured such that the first and second connector members 30, 32 are rotationally engaged to one another in a manner allowing relative rotational movement between the first and second connector members 30, 32 about the rotation axis R. As should be appreciated, the angular orientation of the elongate support member 14 may be adjusted relative to the bone anchor member 16 to a desired angular orientation via rotation of the first connector member 30 relative to the second connector member 32 about the rotational axis R.

Once the select angular orientation between the elongate support member 14 and the bone anchor member 16 has been achieved, the set screw member 18 is advanced along the threaded opening 44 in the first connector member 30 and into compressed engagement with the elongate support member 14. The set screw member 18 urges the elongate support member 14 into abutting engagement against an engagement surface of the first washer member 34, which results in axial displacement of the first washer member 34 into engagement with the second washer member 36, which in turn axially displaces the second washer member 36 toward the second connector member 32 and into compressed engagement with the proximal connecting portion 22 of the bone anchor member 16 positioned within the second passage 42 in the second connector member 32.

Threading the set screw member 18 along the threaded opening 44 in the first connector member 30 serves multiple functions. First, tightening the set screw member 18 against the elongate support member 14 compresses the elongate support member 14 into abutting engagement against the engagement surface of the first washer member 34 to thereby prevent further axial or rotational movement of the elongate support member 14 within the first passage 40. Second, tightening the set screw member 18 also compresses the spline elements 38 defined by the first and second washer members 34, 36 into intermeshing or interdigitating engagement with one another, which in turn selectively prevents relative rotational movement between the washer members 34, 36 and relative rotational movement between the first and second connector members 30, 32, thereby locking the elongate support member 14 and the bone anchor member 16 at a select angular orientation relative to one another. Third, tightening the set screw member 18 also compresses an outer surface of the second washer member 36 against the proximal connecting portion 22 of the bone anchor member 16 positioned within the second passage 42 in the connector member 32, which in turn compressingly engages the proximal connecting portion 22 of the bone anchor member 16 against an inner surface defined by the second passage 42 to substantially prevent further axial or rotational movement of the bone anchor member 16 relative to the connector member 32. Accordingly, a single set screw member 18 is used to secure the elongate support member 14 and the bone anchor member 16 within the passages 40, 42 of the connector members 30, 32, respectively, and to lock the connector members 30, 32 at a select rotational position relative to one another about the rotational axis R, which in turn locks the elongate support member 14 and the bone anchor member 16 at a select angular orientation relative to one another.

Further details regarding the connector assembly 12 can be found in commonly owned U.S. patent application Ser. No. 12/846,298 to Rezach, the contents of which are incorporated herein by references in their entirety. However, it should be understood that the set screw member 18 may be used in association with other types of spinal implant systems. For example, referring to FIG. 3, the set screw member 18 may be used in association with a spinal implant assembly 50 according to another embodiment of the present invention. The spinal implant system 50 is configured to interconnect the elongate support member 14 extending generally along a first longitudinal axis $L_1$ with a bone anchor member 52 extending generally along a second longitudinal axis $L_2$ that is arranged transverse to the first longitudinal axis $L_1$.

In the illustrated embodiment, the bone anchor member 52 generally includes a distal bone engaging portion 54 and a proximal connecting portion 56. In one particular embodiment, the bone anchor member 52 is configured as a bone screw, and more particularly as a pedicle bone screw where the bone engaging portion 54 is configured as a threaded shank including bone engaging threads 58 adapted for anchoring in bone, and where the proximal connecting portion 56 is configured as a U-shaped head including a pair of arm portions 60a, 60b extending axially from a base portion 62 generally along the longitudinal axis $L_2$. The arm portions 60a, 60b together form a U-shaped channel 64 sized and configured to receive the elongate support member 14 therein. A threaded opening 66 defined between the arms 60a, 60b is configured for threading receipt of the set screw member 18. When the elongate support member 14 is positioned within the U-shaped channel 64 in the head portion 56, the set screw member 18 is advanced through the threaded opening 66 and into compressed engagement with the elongate support member 14. The set screw member 18 compresses the elongate support member 14 into abutting engagement against the base portion 62 of the head portion 56, which in turn prevents further axial or rotational movement of the elongate support member 14 within the U-shaped channel 64.

In one embodiment, the head portion 56 of the bone screw 52 may be rigidly and fixedly attached to the threaded shank portion 54 to provide a unitary, single-piece bone screw body. However, in other embodiments, the bone screw 52 may be provided as a poly-axial or multi-axial bone screw where the head portion 56 is rotationally/pivotally attached to the threaded shank portion 54 so as to allow the head portion 56 to pivot and/or rotate relative to the threaded shank portion 54. One example of a poly-axial or multi-axial bone screw is disclosed in commonly owned U.S. Pat. No. 5,879,350 to Sherman et al., the contents of which are hereby incorporated by reference in their entirety. Although a particular type and configuration of the bone anchor member 52 has been illustrated and described herein, it should be understood that other types and configurations of bone anchors are also contemplated for use in association with the present invention.

Referring now to FIGS. 4-7, shown therein are further details regarding the set screw member 18. The set screw member 18 extends along a central longitudinal axis A and generally includes a distal threaded base portion 60, a proximal head portion 62, and a friction member 64 extending distally from the distal end of the threaded base portion 60. The threaded base portion 60 and the head portion 62 of the set screw member 18 may be made from any suitable biocompatible material know to those having ordinary skill in the art, including but not limited to metallic materials such as titanium, titanium alloys, stainless steel, stainless steel alloys, cobalt-chromium, cobalt-chromium alloys, and other metallic alloys, or may alternatively be formed of a non-metallic material. The friction member 64 is formed of a material that is softer (i.e., having a lower hardness value) and/or more flexible or elastic (i.e., more readily deformable) than the material from which the threaded base portion 60 and the head portion 62 are formed. In one embodiment, the friction member 64 is formed of a non-metallic material including but not limited to silicone, plastic, a polymeric material, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), a composite material, a synthetic material, and rubber. In other embodiments, the friction member 64 may be formed of a metallic material including but not limited to superelastic metals or alloys such as, for example, nitinol, or other soft, flexible/elastic, non-rigid metallic materials that would occur to one of ordinary skill in the art.

In the illustrated embodiment, the proximal head portion 62 of the set screw member 18 extends from a proximal end 62a to a distal end 62b and has a cylindrical configuration defining an outer surface profile 66 and an inner passage 68 extending axially through the proximal head portion 62 along the central longitudinal axis A from the proximal end 62a to the distal end 62b. In one embodiment, the outer profile 66 has a hexagonal shape configured for engagement with the distal end portion of a driving tool (not shown) to facilitate application of a rotational force or torque onto the set screw member 18. However, other shapes and configurations of the outer surface profile 66 are also contemplated. In one embodiment, the inner passage 68 is smooth and has a circular shape along its length. However, other shapes and configurations of the inner passage 68 are also contemplated. Additionally, although the illustrated embodiment of the set screw 18 includes a proximal head portion 62, it should be understood that other embodiments are also contemplated wherein the set screw member 18 does not include a proximal head portion 62.

In the illustrated embodiment, the threaded base portion 60 of the set screw member 18 extends from a proximal end 60a to a distal end 60b and has a cylindrical configuration, with the distal end 62b of the head portion 62 attached to the proximal end 60a of the threaded base portion 60 by a reduced strength or frangible portion 70. The reduced strength portion 70 defines a region of reduced strength relative to the adjacent portions 60a, 62b of the threaded base portion 60 and the head portion 62, respectively, to provide a pre-defined fracture initiator or break zone between the threaded base portion 60 and the head portion 62. As should be appreciated, application of a rotational force or torque (or application of a bending or shear force) to the head portion 62 of the set screw member 18 above a threshold level will cause the set screw member 18 to fracture or break along the reduced strength portion 70, thereby allowing selective separation and removal of the head portion 62 from the threaded base portion 60. One example of a set screw having a reduced strength or frangible portion is disclosed in commonly owned U.S. Pat. No. 6,179,841 to Jackson, the contents of which are hereby incorporated by reference in their entirety.

Figure 7:
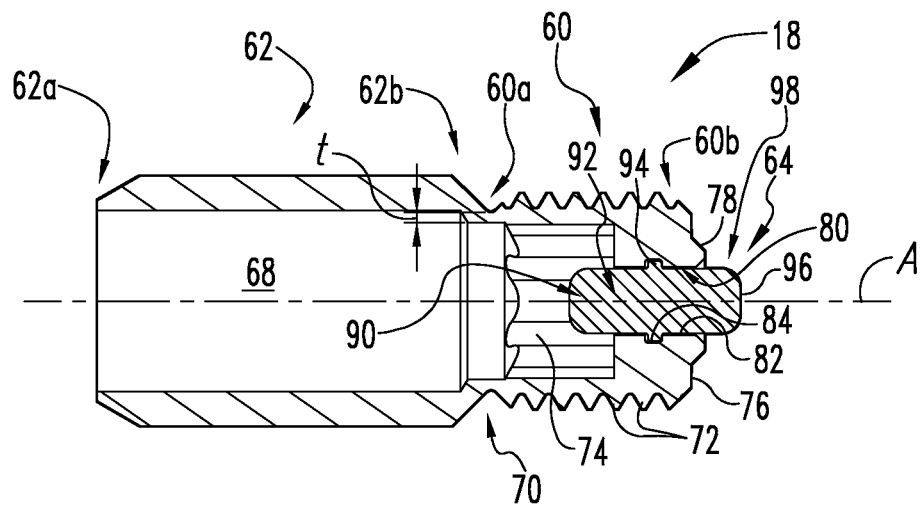
FIG. 7 is a cross sectional side view of the set screw illustrated in FIG. 4, as taken along line 7-7 of FIG. 5.

As illustrated in FIG. 7, in one embodiment, the reduced strength portion 70 has a reduced transverse cross section relative to the adjacent portions 60a, 62b of the threaded base portion 60 and the head portion 62, respectively, to provide the pre-defined fracture initiator or break zone. In one specific embodiment, the reduced strength portion 70 comprises an annular groove extending about the central axis A of the set screw member 18 and positioned between the adjacent portions 60a, 62b of the threaded base portion 60 and the head portion 62, respectively, to define the reduced transverse cross section. In another specific embodiment, the annular groove 70 is defined by an arcuate concave surface extending between the adjacent portions 60a, 62b of the threaded base portion 60 and the head portion 62, respectively. In yet another specific embodiment, the reduced transverse cross section defined by the reduced strength portion 70 is provided by a localized reduction in material thickness t between the adjacent portions 60a, 62b of the threaded base portion 60 and the head portion 62, respectively. Although the illustrated embodiment of the reduced strength portion 70 comprises an annular groove extending about an exterior surface of the set screw member 18, it should be understood that in other embodiments, the annular groove may be provided along an interior surface of the set screw member 18.

Figure 3:
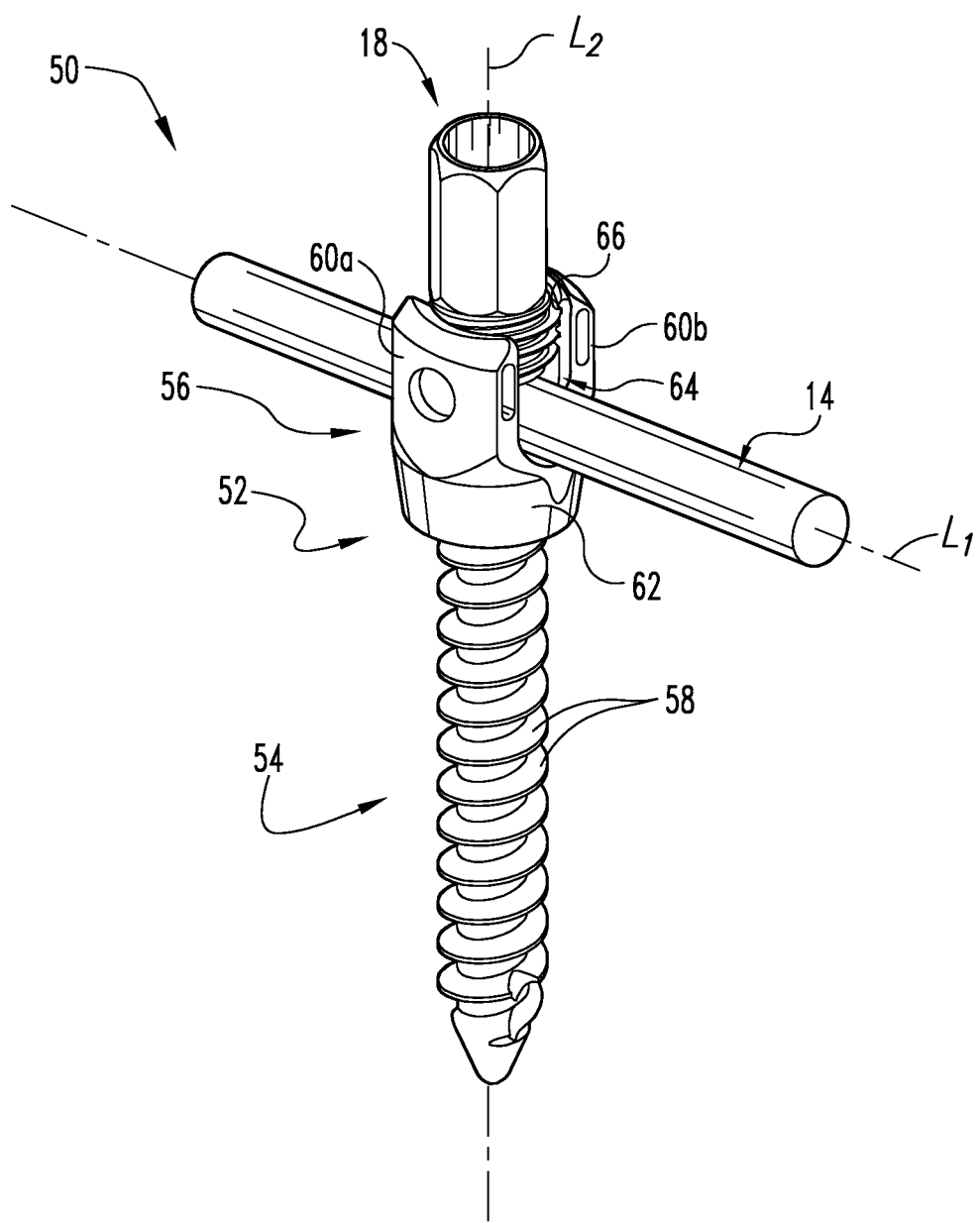
FIG. 3 is a perspective view of another embodiment of a spinal implant system.
Figure 4:
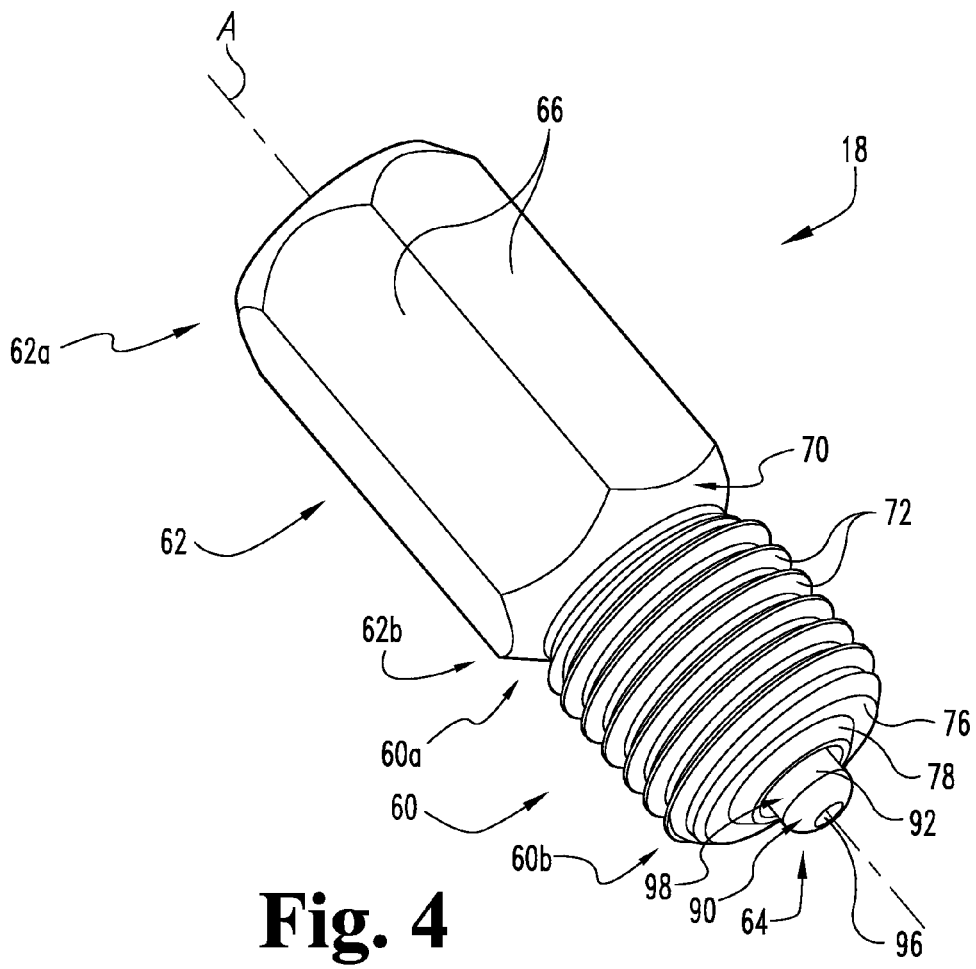
FIG. 4 is a perspective view of one embodiment of a set screw for use in association with the spinal implant systems of FIGS. 1 and 3.
Figure 6:
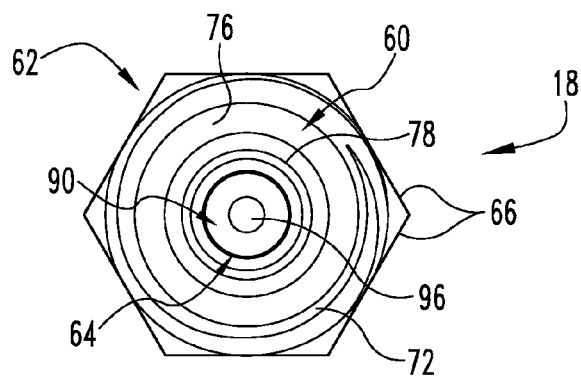
FIG. 6 is an end view of the set screw illustrated in FIG. 4.
Figure 5:
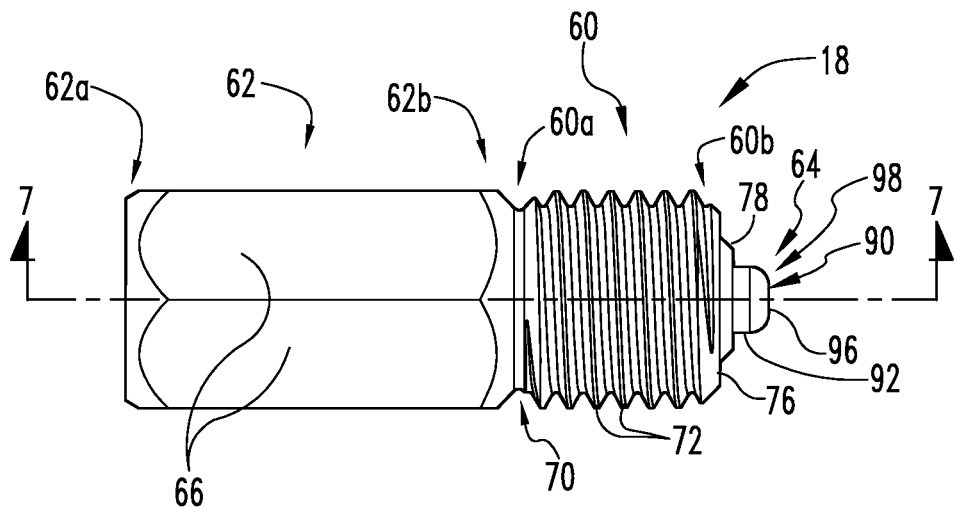
FIG. 5 is side view of the set screw illustrated in FIG. 4.

In the illustrated embodiment, the threaded base portion 60 of the set screw member 18 has a cylindrical configuration defining external threads 72 and an inner recess or receptacle 74 extending axially along the central longitudinal axis A from the proximal end 60*a* toward the distal end 60*b* and configured to receive a distal end portion of a driving tool therein such as, for example, a distal end portion of a screw driver. The external threads 72 formed along the base portion 60 are configured for threading engagement within the threaded opening 44 in the first connector member 30 of the connector assembly 12 (FIGS. 1 and 2) or the threaded opening 66 in the connector head portion 56 of the bone anchor member 52 (FIG. 3). However, other embodiments of the set screw member 18 are also contemplated wherein the threaded base portion 60 is internally threaded for engagement about a connector portion of a spinal implant, or still other embodiments of the set screw member 18 which replace the threads 72 with non-threaded engagement structures such as, for example, ratchet elements.

In the illustrated embodiment, the inner recess 74 has a non-circular cross section configured for engagement with the distal end portion of a driving tool (not shown) to facilitate application of a rotational force or torque onto the threaded base portion 60 of the set screw member 18. In a specific embodiment, the inner recess 74 has a Torx-shaped configuration. However, other shapes and configurations of the inner recess 74 are also contemplated such as, for example, a hexagonal-shaped configuration, a star-shaped configuration, a cross-shaped configuration, a slot-shaped configuration, or other non-circular or polygonal shapes and configurations that would occur to those having ordinary skill in the art. In the illustrated embodiment, the Torx-shaped inner recess 74 extends through over one-half of the length of the threaded base portion 60, although other depths of the inner recess 74 are also contemplated. The threaded base portion 60 also includes a distal face or surface 76 and a central projection 78 extending distally from the distal face 76 and arranged along the central longitudinal axis A. The threaded base portion 60 further defines a friction member receiving passage 80 extending along the central longitudinal axis A from the inner recess 74 to the distal end face of the central projection 78. In one embodiment, the friction member receiving passage 80 includes a circular-shaped inner surface 82 and an annular groove 84 extending into the circular-shaped inner surface 82 and positioned about midway along the depth of the passage 80.

In the illustrated embodiment, the friction member 64 of the set screw 18 comprises an insert plug 90 having a cylindrical configuration and including a circular-shaped outer surface 92 corresponding to the circular-shaped inner surface 82 of the friction member receiving passage 80, and an annular projection 94 extending radially outward from the circular-shaped outer surface 92 and positioned about midway along the length of the cylindrical-shaped plug 90 and corresponding to the shape of the annular groove 84 in the friction member receiving passage 80. The cylindrical-shaped insert plug 90 also includes a generally flat/planar distal end face or pressure surface 96. However, other shapes and configurations of the insert plug 90 are also contemplated, including configurations defining a spherical-shaped distal end face or pressure surface. As illustrated in FIG. 7, the insert plug 90 is positioned within the passage 80 in the threaded base portion 60 of the set screw member 18 with a distal end portion 98 of the insert plug 90 extending axially beyond the distal face 76 and the distal end of the central projection 78. The insert plug 90 is maintained in a select axial position relative to the threaded base portion 60 via close-fitting engagement of the circular-shaped outer surface 92 of the insert plug 90 with the circular-shaped inner surface 82 of the passage 80, and via positioning of the annular projection 94 of the insert plug 90 within the annular groove 84 in the passage 80.

Figure 8:
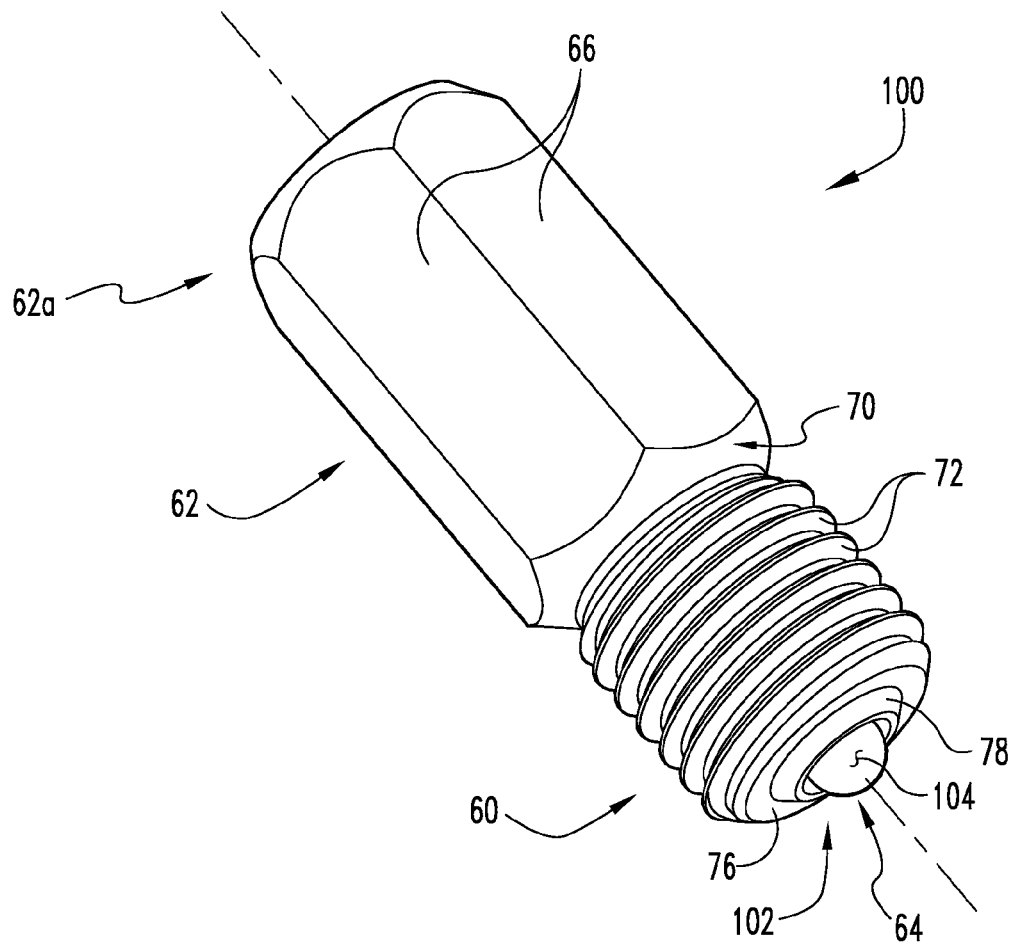
FIG. 8 is a perspective view of another embodiment of a set screw for use in association with the spinal implant systems of FIGS. 1 and 3.

Referring to FIG. 8, shown therein is a set screw member 100 according to another form of the present invention for use in association with a spinal implant assembly. The set screw member 100 is configured similar to the set screw member 18 illustrated in FIGS. 4-7 and described above. Accordingly, like features are indicated using like reference numbers. However, unlike the set screw member 18 which includes a friction member 64 in the form of an insert plug 90 positioned within an axial passage 80 in the threaded base portion 60, the set screw member 100 includes a friction member 64 comprising a quantity or volume of a soft/flexible material (like the material of the insert plug 90) applied to the distal end portion of the threaded base portion 60 to form an insert tip 102 extending axially beyond the distal face 76 and the distal end of the central projection 78. In one embodiment, the material forming the insert tip 102 is applied to a relatively shallow recessed region (not shown) formed in the distal face 76 or the central projection 78 of the threaded base portion 60. The insert tip 102 has a partially spherical configuration including a spherical-shaped distal end face or pressure surface 104. However, other shapes and configurations of the insert tip 102 are also contemplated including cylindrical configurations defining a generally flat/planar distal end face or pressure surface.

Referring once again to FIG. 2, the threaded base portion 60 of the set screw member 18 is threadingly engaged within the threaded opening 44 in the connector member 30 of the connector assembly 12. The threaded base portion 60 is threadingly advanced along the threaded opening 44 until the distal end face or pressure surface 96 of the friction member 64/insert plug 90 is compressed into frictional engagement against the outer surface of the elongate support member 14. Compression of the friction member 64 against the outer surface of the elongate support member 14 in turn deforms the distal end portion 98 of the insert plug 90 and conforms or cups the distal end face or pressure surface 96 into tight fitting and gripping engagement with the elongate support member 14, thereby providing an interference or friction fit between the friction member 64 and the elongate support member 14. The frictional force exerted by the friction member 64 and the resulting tight fitting and gripping engagement between the friction member 64 and the elongate support member 14 prevents or inhibits rotational and translational movement of the elongate support member 14 relative to the connector assembly 12, thereby eliminating the "fiddle factor" or "toggle factor" commonly associated with conventional set screws used in association with spinal fixation/stabilization systems.

As should be appreciated, the soft/flexible nature of the material from which the friction member 64 is formed generates a conforming interference fit or cupping engagement between the friction member 64 and the outer surface of the elongate support member 14, thereby generating increased frictional forces between the friction member 64 and the elongate support member 14 compared to metal-to-metal contact which is prevalent in conventional set screw designs. The conforming interference fit or cupping engagement between the friction member 64 and the elongate support member 14 also tends to reduce the amount of torque that is required to be applied to the set screw member 18 while still providing a similar level of fixation compared to conventional set screw designs. The overall stress exerted onto the connector device (i.e., the connector member 30) and the elongate support member 14 via the set screw member 18 is also reduced. Additionally, the soft/flexible nature of the material from which the friction member 64 is formed does not penetrate or cut into the elongate support member 14, as is often the case with conventional set screw designs. As should be appreciated, the tight fitting and gripping engagement of the friction member 64 with the elongate support member 14 does not mar, knick, dimple, or otherwise damage the elongate support member 14, which might otherwise weaken or negatively affect the structural integrity of the elongate support member 14. Accordingly, the set screw member 18 provides benefits and advantages over conventional set screw designs.

It should be understood that any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. A set screw for use in association with a spinal implant system, comprising:
    a threaded base portion extending along a longitudinal axis, said threaded base portion formed of a first material;
    a proximal head portion extending axially from said threaded base portion; and
    a friction member extending from a distal end of said threaded base portion, said friction member including a projection extending from an outer surface, said friction member formed of a second material different from said first material,
    wherein said set screw includes a first passage extending from said proximal head portion to a portion of said threaded base portion and a second passage extending from said first passage to a distal face of said threaded base portion, said first passage having a first width and said second passage having a second, reduced width, said second passage comprising a groove, said projection being positioned in said groove, and wherein said friction member extends from beyond said distal face, through said second passage and into said first passage.

2. The set screw of claim 1, wherein said second material has a greater degree of flexibility relative to said first material.

3. The set screw of claim 1, wherein said second material has a greater degree of elasticity relative to said first material.

4. The set screw of claim 1, wherein said second material has a lower hardness value relative to said first material.

5. The set screw of claim 1, wherein said first material comprises a metallic material and said second material comprises a non-metallic material.

6. The set screw of claim 5, wherein said second material comprises a silicone material.

7. The set screw of claim 5, wherein said second material comprises a polymeric material.

8. The set screw of claim 7, wherein said polymeric material comprises polyetheretherketone (PEEK).

9. The set screw of claim 5, wherein said first material is selected from a group consisting of a stainless steel material and a titanium material.

10. The set screw of claim 1, wherein said second passage has a circular inner surface and said groove is an annular groove extending into said circular inner surface;
    wherein said outer surface of said friction member is circular and said projection is an annular projection extending radially outward from said circular outer surface; and
    wherein said friction member is maintained within said second passage with said circular outer surface adjacent said circular inner surface and said annular projection within said annular groove.

11. The set screw of claim 1, wherein said first passage has a non-circular cross section configured for engagement with a distal end portion of a driving tool to facilitate application of a rotational force to set screw.

12. The set screw of claim 1, wherein said proximal head portion has a hexagonal shaped outer cross section configured for engagement with a distal end portion of a driving tool to facilitate application of a rotational force to the set screw.

13. The set screw of claim 1, wherein said proximal head portion is attached to said threaded base portion by a region of reduced strength to facilitate selective removal of said proximal head portion from said threaded base portion by a break along said region of reduced strength.

14. The set screw of claim 1, wherein a distal end portion of said friction member is spherical shaped.

15. The set screw of claim 1, wherein said proximal head portion has a width that is greater than the first width.

16. The set screw of claim 1, wherein said friction member has a length extending along the axis between a proximal end and a distal end, said projection being positioned at a midpoint of said friction member between said proximal and distal ends.

17. The set screw of claim 16, wherein said second passage has a length extending along the axis between a first end and a second end, said groove being positioned at a midpoint between said first and second ends of said second passage, and wherein said first end of said second passage being positioned at a midpoint between a proximal end and said distal end of said threaded base portion.

18. A spinal implant assembly, comprising:
    the set screw of claim 1; and
    a connector member including a passage and an opening in communication with said passage; and
    an elongate support member positioned within said passage in said connector member; and
    wherein said set screw is threadedly engaged to said connector member and at least partially positioned within said opening with a distal end portion of said friction member extending into said passage and compressed against an outer surface of said elongate support member to inhibit movement of said elongate support member within said passage.

19. The spinal implant assembly of claim 18, wherein said distal end portion of said friction member includes a distal end surface that is deformed about and substantially conforms to said outer surface of said elongate support member to establish a tight fitting and gripping engagement between said friction member and said elongate support member.

20. The spinal implant assembly of claim 18, wherein said distal end portion of said friction member does not penetrate or cut into said outer surface of said elongate support member.

21. The spinal implant assembly of claim 18, wherein said elongate support member comprises an elongate spinal rod.

22. The spinal implant assembly of claim 18, wherein said connector member is coupled to a bone anchor member configured for engagement to vertebral bone.

23. The spinal implant assembly of claim 22, wherein said bone anchor member comprises a bone screw.

* * * * *